(12) United States Patent
Gohno et al.

(10) Patent No.: US 6,445,764 B2
(45) Date of Patent: Sep. 3, 2002

(54) MULTI-SLICE X-RAY CT APPARATUS AND METHOD OF CONTROLLING THE SAME

(75) Inventors: Makoto Gohno; Masatake Nukui; Tetsuya Horiuchi; Akira Hagiwara, all of Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/747,545

(22) Filed: Dec. 22, 2000

(30) Foreign Application Priority Data

Dec. 27, 1999 (JP) ............................................. 11-371170

(51) Int. Cl.[7] .............................. A61B 6/00; G21K 1/04
(52) U.S. Cl. ......................................... 378/19; 378/150
(58) Field of Search ................................... 378/19, 150

(56) References Cited

U.S. PATENT DOCUMENTS

| | | | | |
|---|---|---|---|---|
| 5,166,961 A | * | 11/1992 | Brunnett et al. | 378/19 |
| 5,684,855 A | * | 11/1997 | Aradate et al. | 378/4 |
| 6,056,437 A | * | 5/2000 | Toth | 378/205 |
| 6,157,696 A | * | 12/2000 | Saito et al. | 378/19 |
| 6,173,031 B1 | * | 1/2001 | Hoffman et al. | 378/19 |
| 6,215,843 B1 | * | 4/2001 | Saito et al. | 378/19 |
| 6,243,438 B1 | * | 6/2001 | Nahaliel et al. | 378/19 |
| 6,259,766 B1 | * | 7/2001 | Cuppen | 378/147 |

* cited by examiner

*Primary Examiner*—Robert H. Kim
*Assistant Examiner*—Allen C. Ho
(74) *Attorney, Agent, or Firm*—Moonray Kojima

(57) ABSTRACT

For the purpose of reconstructing a plurality of X-ray tomographic images having a plurality of practical slice thicknesses while reducing the number of X-ray detector arrays and simplifying configuration, X-rays generated by an X-ray tube 4 are emitted via a slit 15 of a collimator 6 toward a detector 8 disposed opposite to the X-ray tube 4; the length (width) of the collimator 6's slit 15 in the D1 direction and the position of the collimator 6 in the D1 direction are adjustable; the detector 8 is comprised of four X-ray detector arrays; and the widths of the two outer X-ray detector arrays in the D1 direction are larger than the widths of the two center X-ray detector arrays.

18 Claims, 8 Drawing Sheets

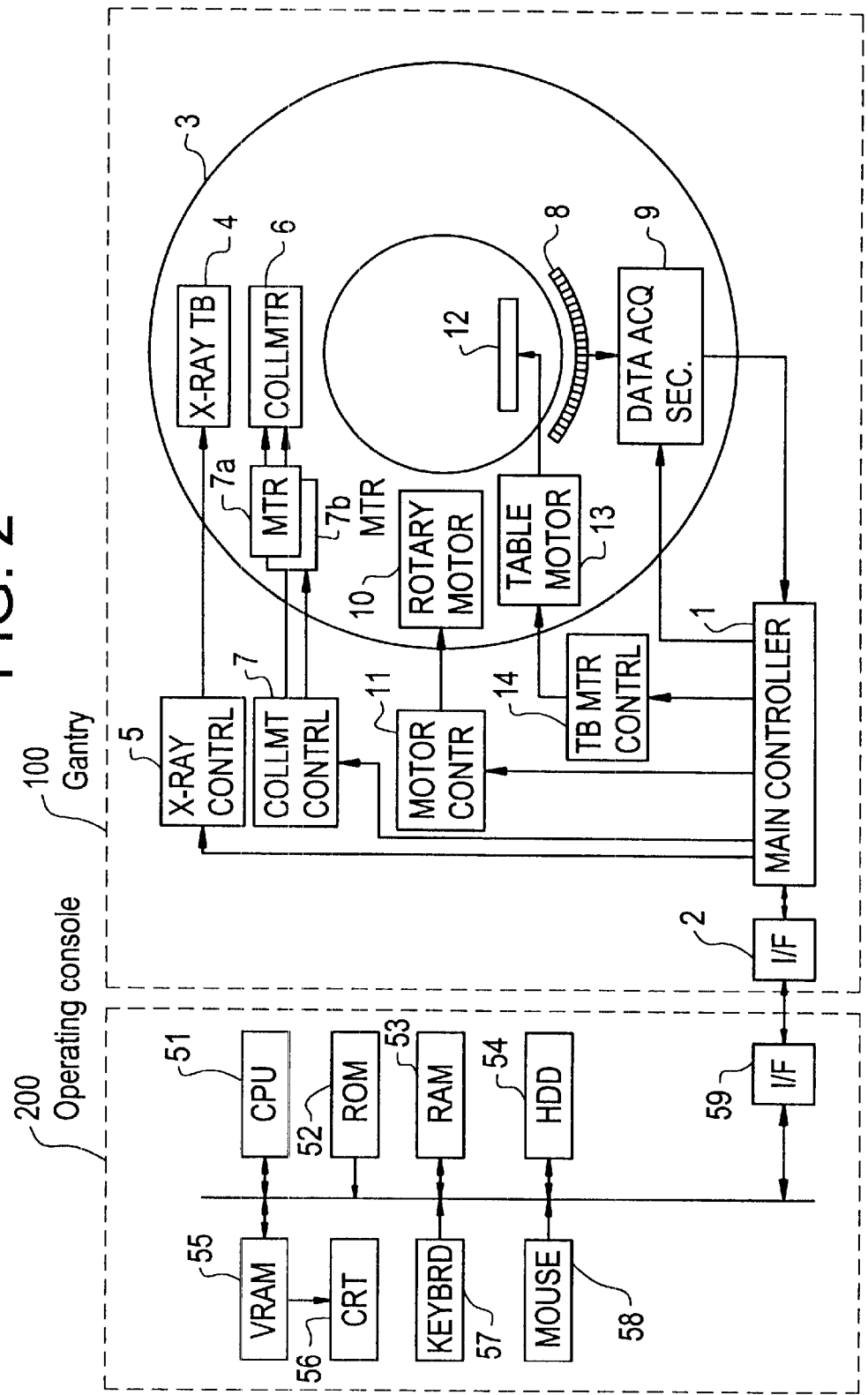

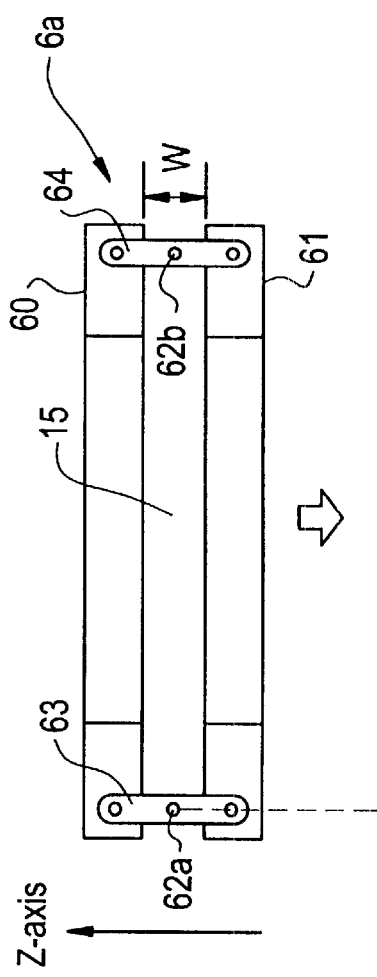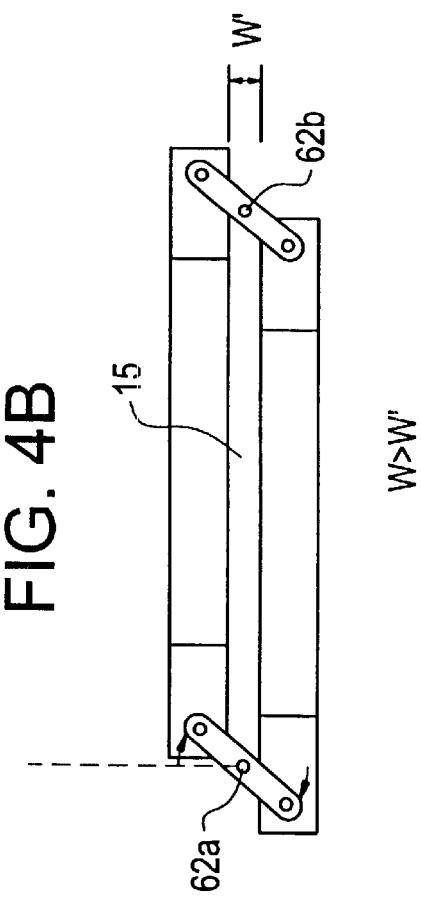

MULTI-SLICE X-RAY CT APPARATUS AND METHOD OF CONTROLLING THE SAME

BACKGROUND OF THE INVENTION

The present invention relates to a multi-slice X-ray CT apparatus and a method of controlling the same for obtaining a plurality of tomographic images of a subject using X-rays.

Generally, in an X-ray CT apparatus for reconstructing a plurality of slice images, a plurality of detectors for detecting an X-ray beam are arranged along the circumference of a "gantry" (each row comprising the plurality of detectors is referred to as an X-ray detector array), and a plurality of the detector arrays are arranged side-by-side in a direction orthogonal to the circumference. The X-ray CT apparatus combines signals detected by the X-ray detector arrays depending upon a specified thickness (slice thickness) to obtain n (four in general) signals in a slice direction.

Recently, there is a need to obtain X-ray tomographic images with different thicknesses by such an X-ray CT apparatus, and in response to the need, the following technique has been developed.

FIG. 1(A) is a diagram illustrating the relationship between a cross section across the plurality of X-ray detector arrays and an X-ray tube. Each X-ray detector array comprises thousands of detector elements along the circumference of the gantry, and the drawing is a cross-sectional view of an i-th channel of the X-ray detector arrays. A total of sixteen X-ray detector arrays (sixteen rows) are shown.

For the sake of simplification, the width of a detector array is assumed to be 1 mm, and the detector arrays are designated as A, B, . . . , P from the left in the drawing.

In this configuration, signals obtained by a group of four consecutive X-ray detector arrays A–D are additively combined by a multiplexer (i.e., a data acquisition section), and signals obtained by groups of the X-ray detector arrays E–H, I–L and M–P are each additively combined in a similar manner. Thus, four X-ray tomographic images each having a thickness of 4 mm can be obtained. Alternatively, by changing the combination of signals, i.e., by combining signals from six adjacent X-ray detector arrays, for example, three X-ray tomographic images each having a thickness of 6 mm can be obtained. In some cases, it is at least possible to obtain X-ray tomographic images having thicknesses of 4 mm, 6 mm, 3 mm, and 3 mm. Such combining is achieved by the multiplexer.

There is another technique in which an open/close controllable collimator is disposed proximate to the X-ray tube, as shown in FIG. 1(B). As shown, the detector comprises two X-ray detector arrays A and B, and the opening of the collimator is controlled to obtain signals with slice thicknesses depending upon the size of the opening.

In the former case (FIG. 1(A)), the multiplexer generates a signal with a slice thickness according to the required combination. Since the multiplexer has a total of sixteen input signals, there are very many combinations for obtaining four X-ray tomographic images by selecting desired signals from the signals, or for obtaining four X-ray tomographic images by combining a plurality of signals. Therefore, the internal configuration of the multiplexer is inevitably highly complicated, and in practice, the multiplexer is configured to handle only a limited number of combinations.

In the latter case, although the slice thicknesses of X-ray tomographic images are variable by opening or closing the collimator, the number of obtainable slices is currently limited to two, and more than two slices cannot be obtained.

It might be attempted to obtain a plurality of X-ray tomographic images having different slice thicknesses by combining the multiplicity of X-ray detector arrays shown in FIG. 1(A) and the collimator control technique shown in FIG. 1(B). However, the number of combinations theoretically depends upon the number of X-ray detector arrays employed, and the configuration of the multiplexer would not be simplified after all.

SUMMARY OF THE INVENTION

The present invention is directed to solving such problems, and provides a multi-slice X-ray CT apparatus and a method of controlling the same which enables a plurality of X-ray tomographic images having a plurality of practical slice thicknesses to be reconstructed by a small number of X-ray detector arrays.

For this purpose, the present invention provides a multi-slice X-ray CT apparatus provided with an X-ray generator and an X-ray detector disposed facing each other with a subject placed therebetween, the X-ray detector having a plurality of detector arrays for detecting X-rays from the X-ray generator, the apparatus rotating the X-ray generator and the X-ray detector to construct X-ray tomographic images having a plurality of slice thicknesses in a direction of conveying the subject, the apparatus comprising a collimator for forming a slit defining a range of X-rays generated by the X-ray detector impinging upon the X-ray detector, and collimator regulating means for regulating the width of the slit corresponding to the direction of conveying the subject, wherein not all the widths of the X-ray detector arrays in the X-ray detector in the direction of conveying the subject are the same.

In accordance with a preferred embodiment of the present invention, the number of X-ray detector arrays in the X-ray detector is four, and the widths of two outer detector arrays in the conveying direction is larger than the widths of two center detector arrays. In this case, it is preferable that the widths of the two center detector arrays be the same, and the widths of the two outer detector arrays be the same. As a result, configuration of the detector section can be simplified, and signals with varied slice thicknesses can be extracted.

Moreover, the collimator regulating means preferably further comprises means for regulating the position of the collimator in the Z-axis direction. As a result, signals for an additional number of slice thicknesses can be extracted.

As can be seen from the above description, and according to the present invention, the total number of X-ray detector arrays can be relatively reduced, and X-ray tomographic images having practical and varied slice thicknesses can be obtained while simplifying configuration.

Further objects and advantages of the present invention will be apparent from the following description of the preferred embodiments of the invention as illustrated in the accompanying drawings.

BRIEF DESCRIPTION OF THE DRAWINGS

FIG. 2 is a diagram illustrating the main configuration of a multi-slice CT apparatus in one embodiment.

FIG. 4 illustrates the configuration and operation of a collimator in one embodiment.

DETAILED DESCRIPTION OF THE INVENTION

Figure 1A:
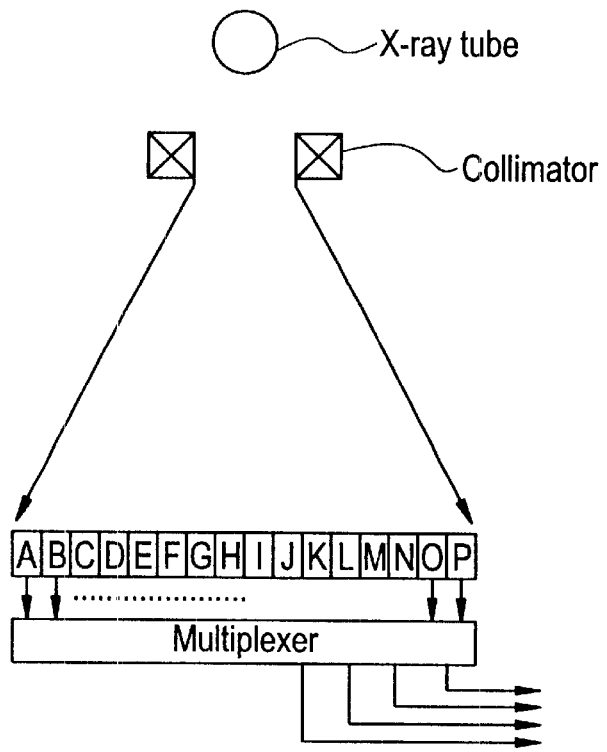
FIG. 1 illustrates the prior art.
Figure 1B:
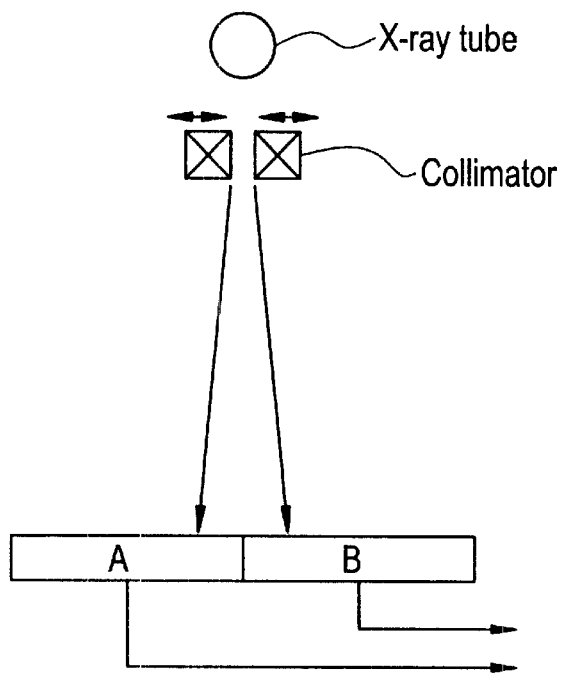

FIG. 2 is a block diagram illustrating the configuration of an X-ray CT system according to one embodiment. The system is comprised of a gantry apparatus 100 for emitting X-rays toward a subject and detecting X-rays passing through the subject, and an operating console 200 for conducting several operative settings of the gantry apparatus 100 and reconstructing an X-ray tomographic image for display based on data output from the gantry apparatus 100.

The gantry apparatus 100 comprises a main controller 1 for exercising overall control.

The gantry apparatus 100 also comprises an interface 2 for communicating with the operating console 200, a gantry 3 having a cavity portion through which the (human) subject rested on a table 12 is conveyed. The gantry apparatus 100 is further provided therein with an X-ray tube 4 serving as an X-ray source (which is driven and controlled by an X-ray tube controller 5), a collimator 6 having a slit for defining a range of impinging X-rays, and two motors 7a and 7b for regulating the slit width of the collimator 6 to define the range of impinging X-rays, and regulating the position of the collimator in the direction of conveying the subject (in the subject's body axis direction), i.e., the position on the Z-axis (the direction perpendicular to the drawing plane). Driving of the motors 7a and 7b is controlled by a collimator controller 7.

The gantry 3 is provided with a detector section 8 for detecting X-rays passing through the subject, and a data acquisition section 9 for acquiring data from the detector section 8. The X-ray tube 4/collimator 6 and the detector section 8 are disposed facing each other across the cavity portion, i.e., across the subject, and are rotated around the gantry 3 while maintaining their relationship. The rotation is operated by a rotary motor 10 driven by a drive signal from a motor controller 11. The table 12 for resting the subject is conveyed in the Z-axis direction by a table motor 13.

The main controller 1 analyzes various commands received via the interface 2, and outputs based on the analysis several control signals to the X-ray tube controller 5, collimator controller 7, motor controller 11, table motor controller 14 and data acquisition section 9. (Detailed description on the control over the data acquisition section 9 will be made later.) The main controller 1 also executes a process for transmitting data acquired at the data acquisition section 9 via the interface 2 to the operating console 200.

The operating console 200 is a so-called workstation, and comprises a CPU 51 for exercising control over the entire apparatus, a ROM 52 which stores a boot program and a BIOS, and a RAM 53 serving as a main storage device, as shown in FIG. 2.

The operating console 200 also comprises an HDD 54 which is a hard disk device and stores an OS and a diagnostic program for supplying various instructions to the gantry apparatus 100 and for reconstructing an X-ray tomographic image based on data received from the gantry apparatus 100. The operating console 200 also comprises a VRAM 55 which is a memory for mapping image data to be displayed, and a CRT 56 for displaying an image based on the image data etc. mapped on the VRAM 55. The operating console 200 further comprises a keyboard 57 and a mouse 58 for operating various settings, and an interface 59 for communicating with the gantry apparatus 100.

The configuration of an X-ray CT system according to one embodiment has been generally described in the preceding paragraphs. Next, the configuration and operation of the X-ray tube 4, collimator 6 and detector section 8 will be described in more detail with reference to FIGS. 3–5.

Figure 3:
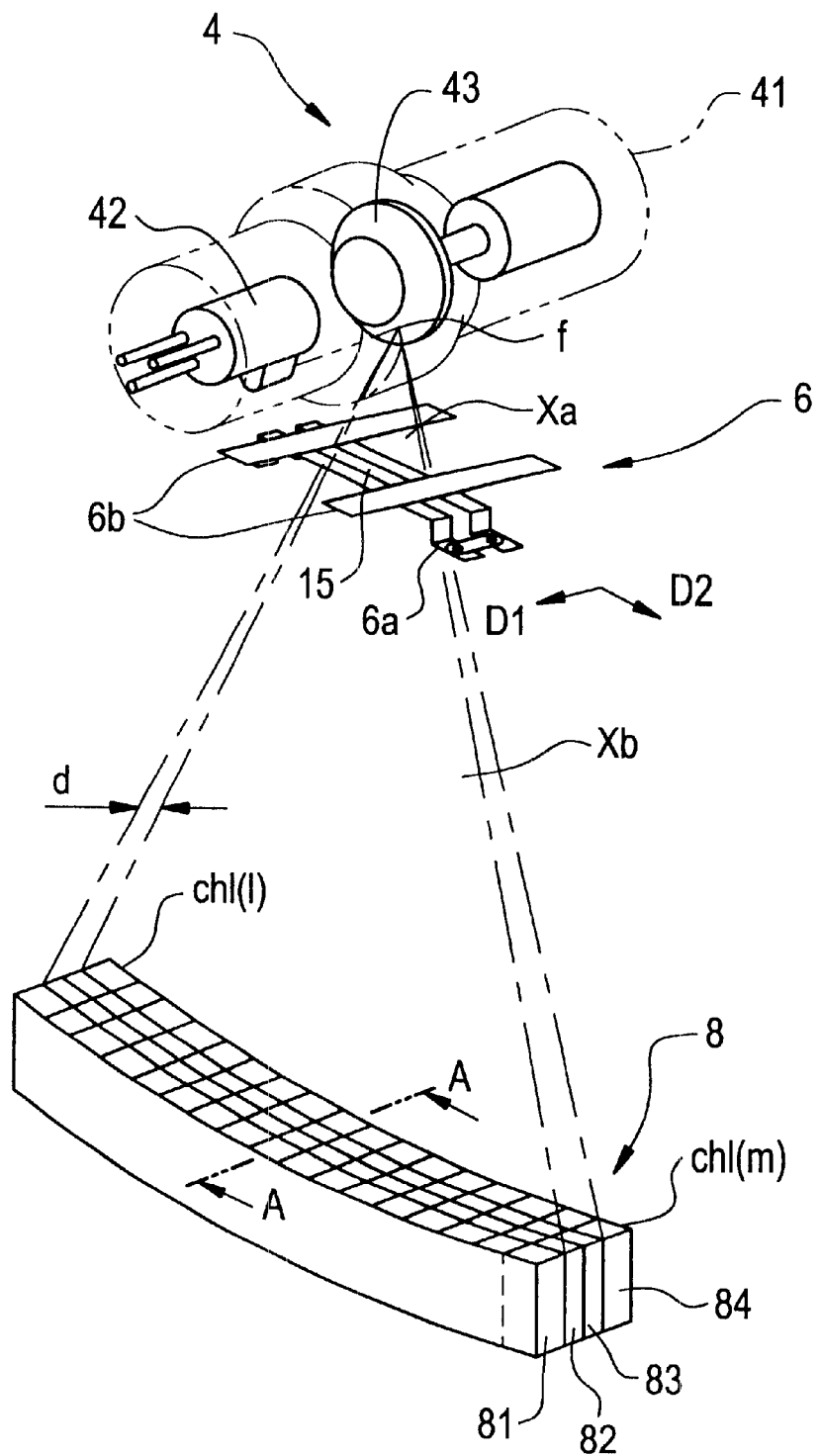
FIG. 3 illustrates the configuration around an X-ray tube and detector.

FIG. 3 illustrates the configuration of main portions of the X-ray tube 4, collimator 6 and detector section 8.

The X-ray tube 4 has a cathode sleeve 42 containing therein a focusing electrode and a filament, and a rotary target 43, both inside of a housing 41, and emits X-rays Xa from a focus f.

The collimator 6 is made of an X-ray screening material (lead, tungsten or the like), and is comprised of a collimator 6a (which will be described in more detail later) for defining in the Z-axis direction (D1 direction in FIG. 3) a range of impinging X-rays emitted from the X-ray tube 4, and a collimator 6b disposed between the collimator 6a and the X-ray tube 4 and comprised of two fixed screening plates for defining a range of impinging X-rays (fan angle) in the longitudinal direction of the detector 8. The collimators 6a and 6b form a slit 15 (an X-ray emitted range, or a gap through which X-rays pass). In one embodiment, the width of the slit 15 in the Z-axis direction (D1 direction in FIG. 3) is variable by mechanical operation of the collimator 6a. Moreover, the collimator 6a is movable and adjustable in the Z-axis direction in its entirety. These operations are enabled by the motors 7a and 7b shown in FIG. 2. Those skilled in the art will easily recognize that the positional change of the collimator 6a in the Z-axis direction can be implemented by the motor 7a. Therefore, adjustment of the slit width by the collimator 6a will be described here with reference to FIG. 4.

FIG. 4(a) is a top plan view of the collimator 6a (as viewed from the direction of the X-ray tube 4).

As shown, the collimator 6a is comprised of two screening plates 60 and 61, and link rods 63 and 64 for linking the ends of the screening plates 60 and 61. The link rods and the screening plates are pivotally connected so that the rods and plates can be rotated with respect to each other. The rods 63 and 64 have the same length, and therefore, the screening plates 60 and 61 can be maintained in parallel with each other. The link rods 63 and 64 are provided with respective pivot shafts 62a and 62b at their centers, and the rods 63 and 64 can be rotated around the pivot shafts 62a and 62b driven by the motor 7a.

Thus, it will be appreciated that when the pivot shafts 62a and 62b are rotated clockwise, the screening plates 60 and 61 gradually come close to each other while maintained in parallel. In other words, the gap between the screening plates 60 and 61 defines the opening width of the slit 15 in the Z-axis direction, hence, the width d of impinging X-rays in FIG. 3. (The opening width of the slit 15 in the Z-axis direction will be referred to simply as a slit width hereinbelow.)

Moreover, since the rods 63 and 64 are provided with the pivot shafts 62a and 62b at their centers, the position of the centerline of the slit can be successfully fixed regardless of the rotation angle of the pivot shafts 62a and 62b.

As mentioned earlier, the collimator, in one embodiment, can be moved in the Z-axis direction in its entirety. This movement is operated by the motor 7b. Since the slit width d is only varied with respect to the centerline that connects the pivot shafts 62a and 62b at the centers of the rods 63 and 64, the movement of the whole collimator in the Z-axis direction can be controlled with respect to the position of the centerline of the slit, i.e., the Z-position of the line connecting the pivot shafts 62a and 62b. The control can thus be simplified.

More particularly, assuming that the screening plate 60 is fixed, the other screening plate 61 should move. Then, the centerline of the slit will be varied depending upon the position of the screening plate 61, i.e., the centerline will not be fixed. Since the present embodiment is characterized in one aspect that the movement of the whole collimator in the Z-axis direction is controlled as described above, if one screening plate is fixed and only the other screening plate is moved, the amount of movement of the whole collimator in the Z-axis direction must be calculated taking the slit width into consideration.

Here, the rods 63 and 64 are provided with the pivot shafts 62a and 62b at their centers, and both the screening plates 60 and 61 approach or depart from each other with respect to the centerline. Thus, movement control of the whole collimator in the Z-axis direction can be simplified.

Returning to FIG. 3, the detector section 8, in one embodiment, is comprised of four X-ray detector arrays 81–84, and each X-ray detector array has m (=1,000 in one embodiment) detector cells. That is, the detector section 8 comprises 1st–m-th channels for obtaining detected signals. Moreover, the widths of the outer X-ray detector arrays 81 and 84 in the D1 direction (the Z-axis direction) are larger than those of the center detector arrays 82 and 83.

Figure 5:
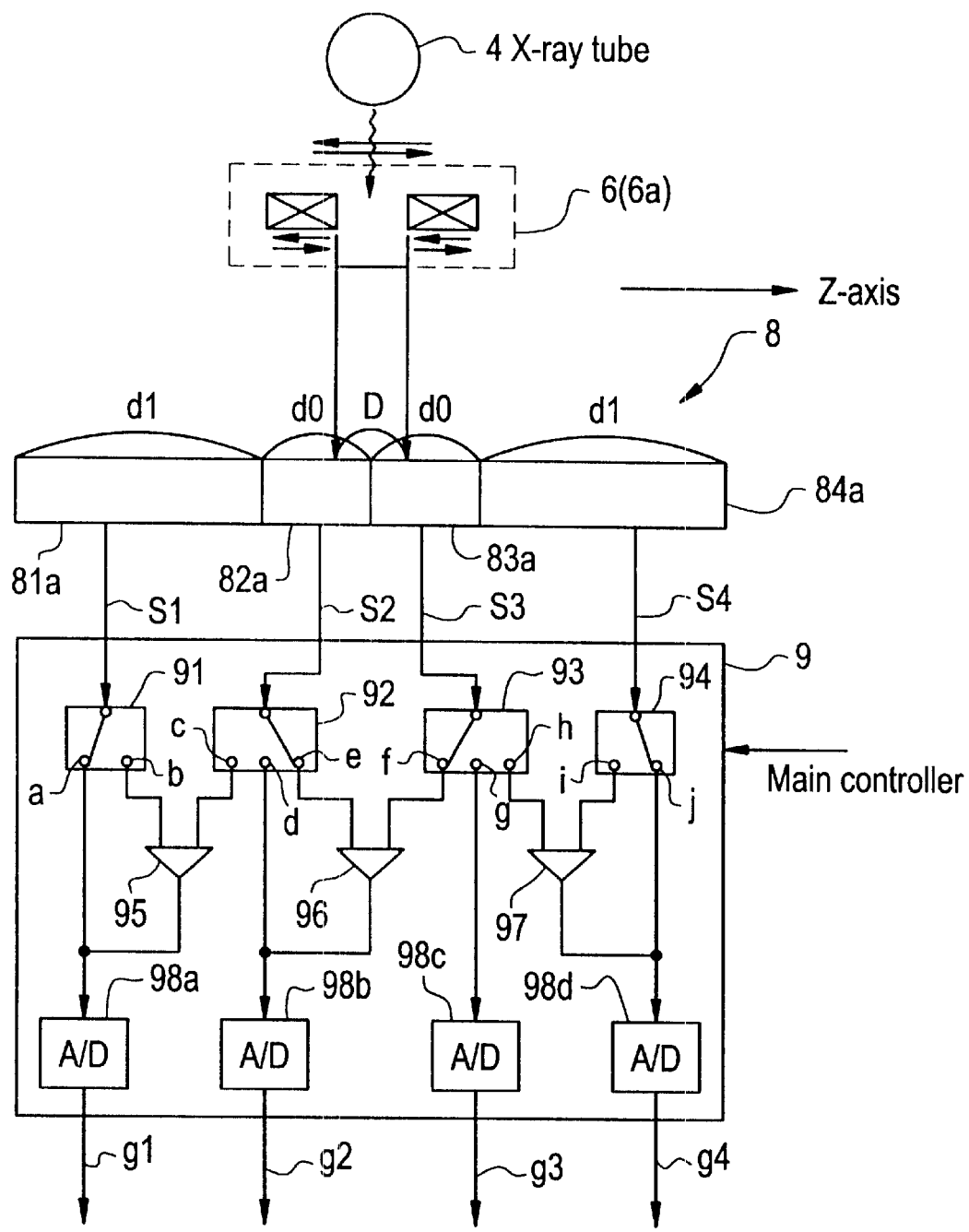
FIG. 5 illustrates the circuit configuration of a data acquisition section 9 and its peripheral connections in one embodiment.

The relationship between the cross section as viewed from the A-A direction in the configuration of FIG. 3 and the circuit configuration in the data acquisition section 9 is schematically shown in FIG. 5.

FIG. 5 shows the configuration at a channel (i) in the detector section 8. Each reference numeral 81a, 82a, 83a and 84a designates a cell (channel i) in the corresponding X-ray detector array 81–84.

In the drawing, the symbol "D" represents the width of emitted X-rays that reach the detector section 8 through the slit of the collimator 6 (strictly, the collimator 6a).

The data acquisition section 9 is configured as combining means comprised of analog switches 91–94, adders 95–97 (comprised of operational amplifiers etc.) and A/D converters 98a–98d, for additively and selectively combining signals detected by the adjacent X-ray detector arrays. Choice of switches (i.e., in which of modes the switches operate; the modes will be described later) is based on control command signals from the main controller 1. The switch 91 chooses one of terminals a and b; the switch 92 chooses one of terminals c, d and e; the switch 93 chooses one of terminals f, g and h; and the switch 94 chooses one of terminals i and j.

If signals supplied from the cells to the data acquisition section 9 are designated as s1–s4, and the result of addition is represented as (x+y), in which two signals input to an adder are represented as x and y, then signals g1–g4 output from the data acquisition section 9 in the illustrated condition can be expressed as follows:

$g1=s1$; $g2=s2+s3$; $g3=$IGNORE; and $g4=s4$, wherein "IGNORE" indicates that a signal is not available, or the signal is regarded as invalid.

Similarly, and for example, if the switches 91, 92, 93 and 94 are shifted to the terminals a, d, g and j, respectively, it will be easily recognized that the signals g1–g4 are expressed as follows:

$g1=s1$; $g2=s2$; $g3=s3$; and $g4=s4$.

It should be noted that the signals g1 and g4 are substantially not available when X-rays do not impinge upon at least the outer cells, as shown in FIG. 5.

The obtained signals g1–g4 are then transferred to the operating console 200 (see FIG. 2) as digital data of the i-th channel. The operating console 200 temporarily stores the data transferred from all the channels, and these operations are repeated for each rotation of the gantry. When required data (i.e. data needed for image reconstruction) have been stored, an X-ray tomographic image is reconstructed and the image is displayed on the CRT 56. Since the slit width of the collimator 6 and the position of the whole collimator in the Z-axis direction are specified at the operating console 200, the operating console 200 knows in advance which data is valid or invalid among the four received data g1–g4, and which data represents a slice thickness of what number of millimeters.

Therefore, the X-ray CT apparatus of such configuration provides a plurality of X-ray tomographic images in the Z-axis direction of the subject.

Based on the configuration in the preceding description, a typical example of scanning by the multi-slice X-ray CT system in one embodiment will now be described hereinbelow.

In the description below, it is assumed that the width d1 of the X-ray detector arrays 81 and 84 in the Z-axis direction is 7.5 mm, and the width d0 of the center X-ray detector arrays 82 and 83 is 2.5 mm. That is, the total width in the Z-axis direction, which is the sum of the four X-ray detector arrays, is 7.5×2+2.5×2=20 mm.

FIG. 6 exemplarily shows the slice thickness and the number of slices detectable when the center of the collimator coincides with the center of the detector 8 (i.e., the boundary between the X-ray detector arrays 82 and 83). In the drawing, the A/D conversion is omitted because it suffices to show the additive relationship of the signals.

Figure 6A:
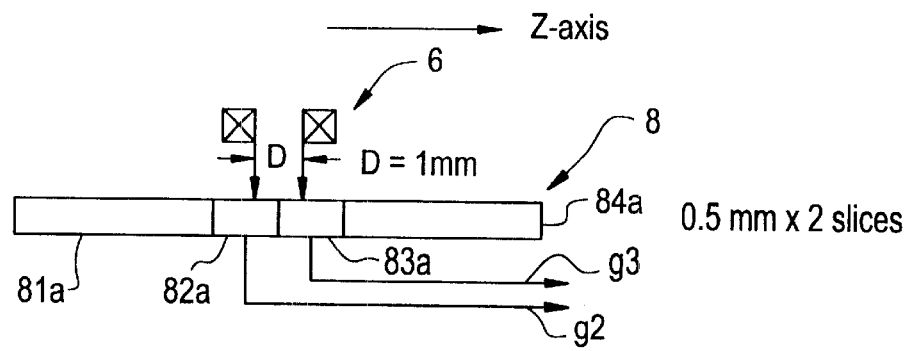
FIGS. 6 and 7 exemplarily illustrate operation in one embodiment.

FIG. 6(a) exemplarily shows a mode in which the width D of impinging X-rays is 1 mm, and signals detected by the cells are output unchanged. If the mode is described in terms of the switches 91–94 in FIG. 5, it can be regarded as the switches 91, 92, 93 and 94 choosing the terminals a, d, g and j, respectively.

In this case, the width D of X-rays impinging upon the X-ray detector arrays is 1 mm, and the centerline of the emitted X-rays coincides with the boundary between the X-ray detector arrays 82 and 83. Therefore, FIG. 6(a) shows that the detected signals g1 and g4 are regarded as invalid, and the signals g2 and g3 are valid signals of slices adjacent in the Z-axis direction each having a thickness of 0.5 mm.

It will be easily recognized that, if the switch state in the data acquisition section 9 remains the same and the width D of impinging X-rays is set equal to or less than 5 mm by controlling the collimator 6, then two slices each with a thickness of D/2 mm are obtained.

Figure 6B:
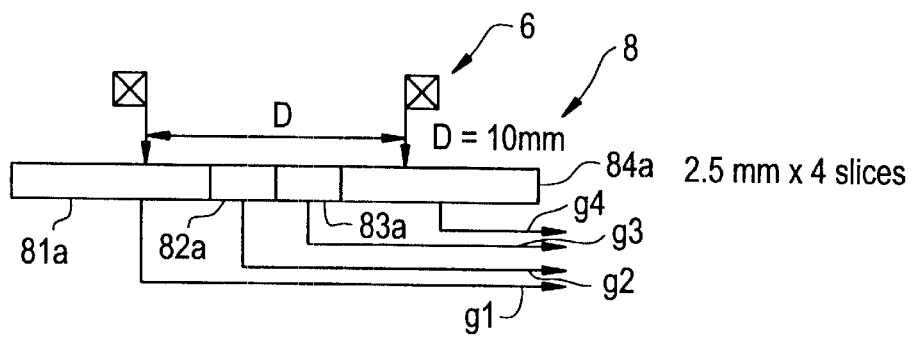
Figure 6C:
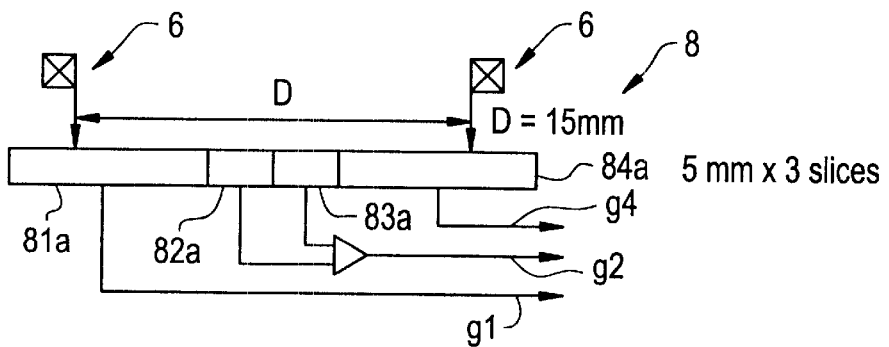
Figure 6D:
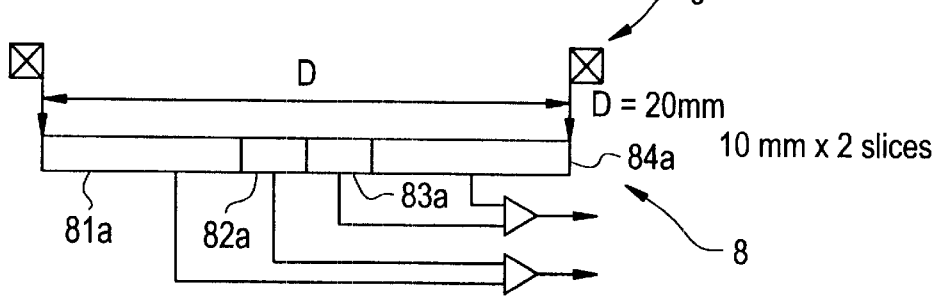

Referring next to FIG. 6(b), there is exemplarily shown a width D of impinging X-rays of 10 mm, in which the switch state (i.e., mode) in the data acquisition section 9 is the same as that shown in FIG. 6(a).

According to such a condition, X-rays impinge upon a region with a thickness of 2.5 mm in the cell 81a (the i-th channel in the X-ray detector array 81), the entire region of the cells 82a and 83a (the i-th channels in the X-ray detector arrays 82 and 83), and a region with a thickness of 2.5 mm in the cell 84*a* (the i-th channel in the X-ray detector array 84). The width of the X-ray detector arrays 82 and 83 is 2.5 mm, and consequently, four slices each of a thickness of 2.5 mm are obtained.

If the width D of impinging X-rays is in a range of 5–20 mm (a case of no more than 5 mm has been explained with reference to FIG. 6(*a*)), signals can be obtained of slices continuous in the Z-axis direction having thicknesses of D/2–2.5 mm, 2.5 mm, 2.5 mm, and D/2–2.5 mm.

FIG. 6(*c*) exemplarily shows a mode in which the width D of impinging X-rays is 15 mm, and signals from the two center cells are additively combined. If the mode is described in terms of the switches 91–94 in FIG. 5, it can be regarded as the switches 91, 92, 93 and 94 choosing the terminals a, e, f and j, respectively. In this case, since no input signals are supplied for producing the signal g3 in FIG. 5, the operating console 200 (CPU 51) regards the data of signal g3 as invalid, and reconstructs respective X-ray tomographic images according to data of the three other valid signals g1, g2 and g4.

Returning to FIG. 6(*c*), X-rays impinge upon a region with a thickness of 5 mm in the X-ray detector array 81, the entire region of the X-ray detector arrays 82 and 83, and a region with a thickness of 5 mm in the X-ray detector array 84. Signals from the detector cells 82*a* and 83*a* are added by the adder 96, and consequently, three slices each with a thickness of 5 mm are obtained.

Thus, when signals of the two center X-ray detector arrays 82*a* and 83*a* are added, one slice having a thickness D of impinging X-rays is obtained when the thickness D of impinging X-rays is no more than 5 mm, and three slices continuous in the Z-axis direction having thicknesses of D/2–2.5 mm, 5 mm, and D/2–2.5 mm are obtained when the thickness D of impinging X-rays is more than 5 mm.

FIG. 6(*d*) exemplarily shows a mode in which the width D of impinging X-rays is 20 mm, and signals from paired adjacent outer and inner cells are additively combined. If the mode is described in terms of the switches 91–94 in FIG. 5, it can be regarded as the switches 91, 92, 93 and 94 choosing the terminals b, c, h and i, respectively. In this case, since no input signals are supplied for producing the signals g2 and g3 in FIG. 5, the operating console 200 (CPU 51) regards the data of signals g2 and g3 as invalid, and reconstructs respective X-ray tomographic images according to data of two other valid signals g1 and g4.

Returning to FIG. 6(*d*), X-rays impinge upon all the cells, and the signal g1 is supplied with the result of addition of signals from the cells 81*a* and 82*a* via the adder 95, and the signal g4 is supplied with the result of addition of signals from the cells 83*a* and 84*a* via the adder 97. Consequently, two slices continuous in the Z-axis direction each having a thickness of 10 mm are obtained.

Thus, when cells 81*a* and 82*a* in the X-ray detector arrays 81 and 82 are added and cells 83*a* and 84*a* in the X-ray detector arrays 83 and 84 are added, two adjacent slices each having a thickness of D/2 mm can be obtained in any range within 0<D≦20 mm.

In the embodiments described above, the widths of the X-ray detector arrays having the aforementioned relationship, in combination with control over the collimator, allows the switches in the data acquisition section 9 (multiplexer) to have a very simple circuit configuration, and yet signals with great variety in slice thickness and great variety in number of slices can be obtained compared with the case of a detector section simply comprised of four X-ray detector arrays of equal thickness.

The above description assumes that the center of the collimator 6's slit in the Z-axis direction coincides with the center of the detector section 8 in the Z-axis direction (i.e. the boundary between the X-ray detector arrays 82 and 83), and does not take into account movement of the entire collimator in the Z-axis direction driven by the motor 7*b*.

A case of regulating movement of the entire collimator 6 in the Z-axis direction will therefore next be described with reference to FIG. 7, giving examples of obtaining several combinations of additional slice thicknesses. When the center of the collimator 6's slit is positioned at the center of the detector section 8, as in FIG. 6, the collimator 6 is referred to as being at a home position.

Figure 7A:
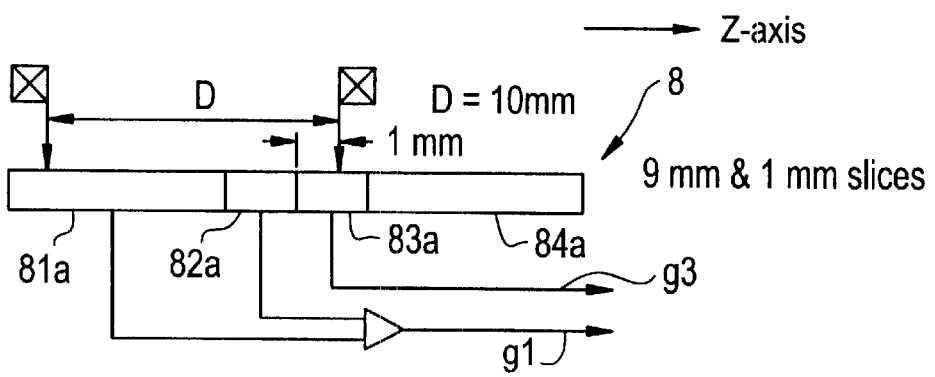
Figure 7B:
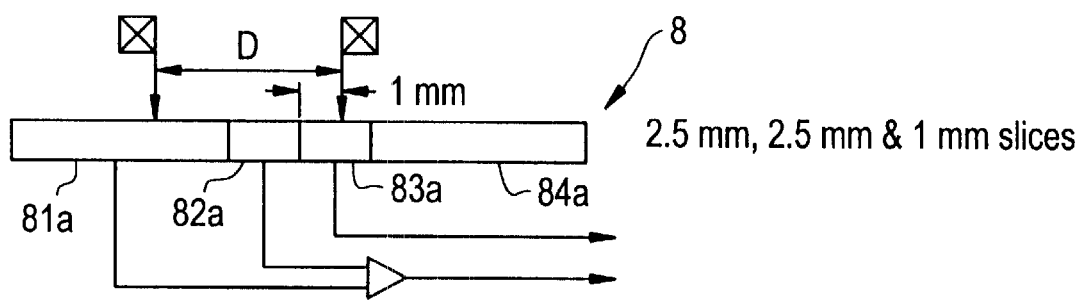

FIG. 7(*a*) shows the collimator 6 moved by 4 mm in the Z-axis direction from the home position by driving the motor 7*b*, and the width D of impinging X-rays set to 10 mm by driving the motor 7*a*. That is, the width of impinging X-rays is 1 mm in the Z-direction of the X-ray detector array 83, and the width of X-rays impinging upon the X-ray detector 81 is 10−(2.5+1.0)=6.45 mm.

Moreover, signals from the cells 81*a* and 82*a* are added. If this condition is described in terms of the switches 91–94 in FIG. 5, it can be regarded as the switches 91, 92, 93 and 94 choosing the terminals b, c, g and j, respectively. Since X-rays do not impinge upon the cell 84*a*, only the signals g1 and g3 are substantially valid of signals output from the data acquisition section 9.

As shown, since the signal g1 is finally the result of addition by the adder 98*a*, the signal is for a slice having a thickness of 9 mm, and the signal g3 is for a slice having a thickness of 1 mm. This combination of slice thicknesses cannot be obtained when the collimator 6 is at the home position (see FIG. 6).

FIG. 7(*b*) shows the collimator 6 moved by 2 mm in the Z-axis direction from the home position, and the width D of impinging X-rays set to 6 mm by driving the motor 7*a*. Here, signals from the cells are not added. Since the switch settings in the data acquisition section 9 are the same as those shown in FIG. 6(*b*), they will not be further described.

In this case, X-rays impinge upon a region with a thickness of 2.5 mm in the cell 81*a*, the entire region in the cell 82*a* (2.5 mm), and a region with a thickness of 1 mm in the cell 83*a*. Therefore, the signals g1–g3 are for slices having thicknesses of 2.5 mm, 2.5 mm and 1 mm.

In the embodiments described above, four X-ray detector arrays are provided in the X-ray detector section, the cell width of the two center X-ray detector arrays is made smaller than that of the two outer X-ray detector arrays, and the width of the collimator's slit in the Z-axis direction is regulated. Therefore, a great variety of slices can be obtained compared to the case of using a detector section in which the same number of X-ray detector arrays of equal thickness are arranged.

In other words, the conventional technique has required more than four X-ray detector arrays and a multiplexer in a data acquisition section having more complicated configuration to obtain slices equivalent to the variety of slices as described in the above embodiments. In the above embodiments, the number of the X-ray detector arrays can be reduced, and hence the configuration of the multiplexer can be simplified.

Especially, the collimator is allowed to move in the Z-direction, resulting in an evident difference from the conventional technique.

Moreover, and in general, as the number of X-ray detector arrays in the detector section of a multi-slice X-ray CT system increases, the higher is the incidence of manufacturing defects in the detector section. For example, the aforementioned conventional technique is exemplified by an X-ray detector comprising sixteen X-ray detector arrays, and, simply calculated, the incidence of defective X-ray detectors is four times that in the X-ray detector in the embodiments of the present invention. In the above embodiments, since the number of X-ray detector arrays is very small, a good yield can be achieved in manufacture and the configuration can be simplified, thereby enabling a reduction in manufacturing cost greater than would be expected from the difference in the number of X-ray detector arrays.

Although the above embodiments are exemplified by four X-ray detector arrays in the detector section, the number of arrays may be more than four. The main point is that the slit width of the collimator is made adjustable and n X-ray detector arrays are provided with unequal widths, whereby a greater variety of slice thicknesses can be secured compared with a simple configuration having n equivalent X-ray detector arrays. In other words, the same kinds of slice thickness as those provided by n X-ray detector arrays of equal width can be secured with a much smaller number of X-ray detector arrays.

Operation of the switches in the data acquisition section 9 and control of the slit width and position by the collimator are effected by, for example, making a selection from a menu displayed on the CRT 56 in the operating console 200. The menu may display a list of sets of detectable slice thicknesses and corresponding number of such slices. After the selection, specific control commands corresponding to the switches 91–94 are generated to achieve the selected slice thicknesses and number, and the commands are output to the gantry apparatus 100. Then, a command to start a scan can be output.

Since the CPU 51 in the operating console 200 knows which of g1–g4 in the data transferred from the gantry apparatus 100 are valid or invalid (it is of course possible that all of the data are valid) at this time, the CPU 51 stores the valid data in the HDD 54 serving as an external storage device, and executes an image reconstruction process.

Moreover, the main controller 1 in the gantry apparatus 100 interprets instruction commands from the operating console 200 as described earlier, issues respective control command signals to the X-ray tube controller 5, collimator controller 7, motor controller 11, table controller 14 and data acquisition section 9, and sequentially transfers data of the channels in the X-ray detector arrays obtained from the data acquisition section 9 to the operating console 200.

Figure 8:
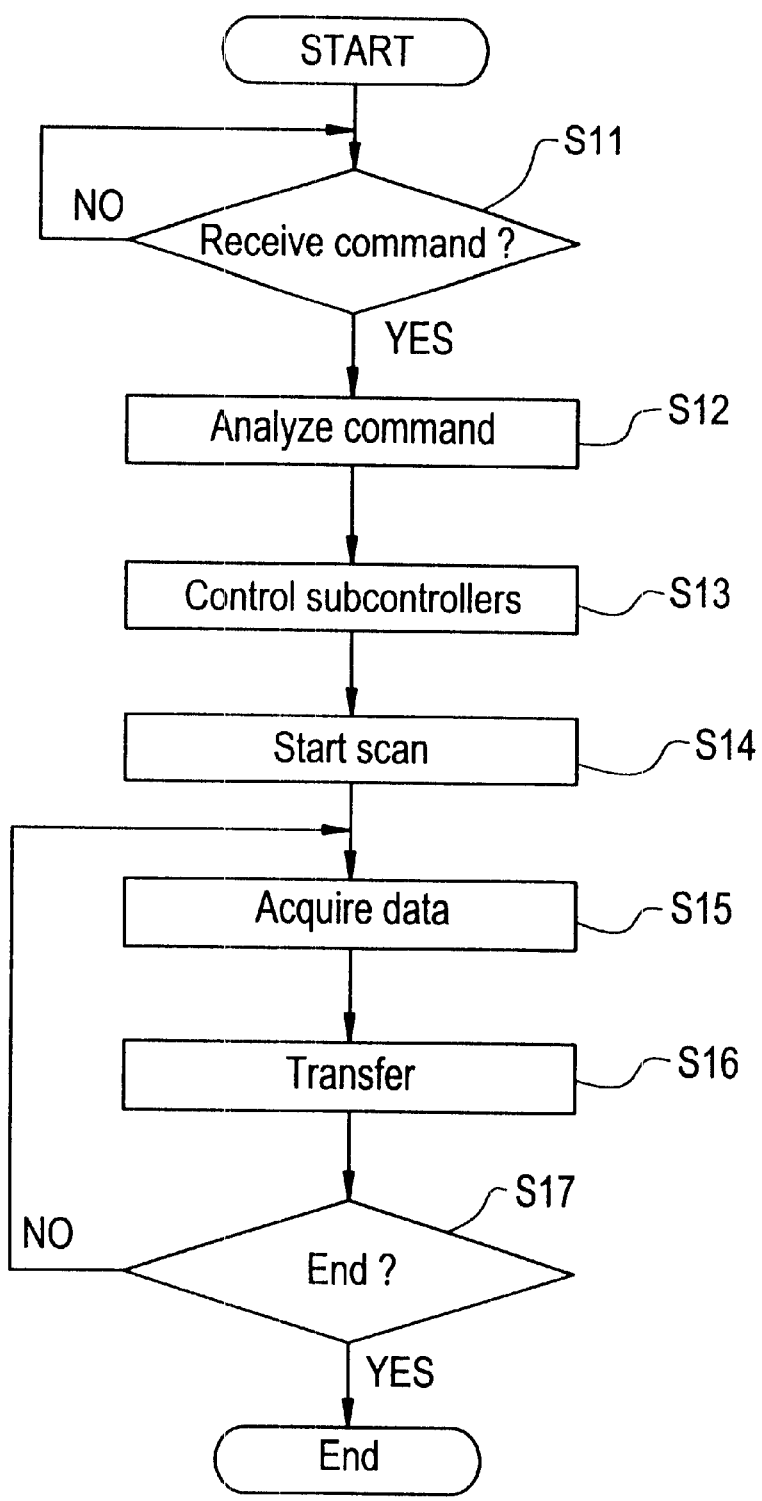
FIG. 8 is a flow chart illustrating an operative processing procedure of a main controller in one embodiment.

A processing procedure by the main controller 1 in the gantry apparatus 100 is specifically shown in the flow chart of FIG. 8.

First, preparation is made for receiving a command from the operating console at Step S11. Upon receiving, the command, which contains several parameters pertaining to a scan, is analyzed at Step S12, and a process is executed to generate control signals for the X-ray tube controller 5, collimator controller 7, motor controller 11, table controller 14 and data acquisition section 9 at Step S13. Control signals representing the slit width of the collimator 6, its position in the Z-axis direction and control over the switches in the data acquisition section 9 are also generated here. Then, an actual scan is started at Step S14.

Next, a loop process including Steps S15–S17 is entered, and a process is executed for transferring the data obtained at the data acquisition section 9 to the operating console. In Step S17, if there is "NO", then Step S15 is reinstituted. On the other hand, if there is "YES", then Step S18 is entered to end the process.

The operating console performs an image reconstruction process and the like following the known procedure as described earlier.

In the embodiments described above, the width of the two center X-ray detector arrays of the four X-ray detector arrays in the detector section 8 is made smaller than that of the two outer X-ray detector arrays. This is so that the number of slices can be increased even when the collimator is placed near the home position and the width of impinging X-rays is relatively large (D>5 mm in the above embodiments), thereby enriching variation.

Moreover, In the above embodiments, detected signals to be transferred to the operating console are four signals g1–g4 in the Z-axis direction. However, the number of the signals is currently determined in light of the transfer speed in state-of-art computer architecture and the processing speed for image reconstruction in the operating terminal, and the present Invention is not limited thereto. If a faster interface and a faster processing terminal are developed in the future, the number of data signals to be transferred should be more than four. Accordingly, the present invention is not limited to the embodiments described above.

Many widely different embodiments of the invention may be configured without departing from the spirit and the scope of the present invention. It should be understood that the present invention is not limited to the specific embodiments described in the specification, except as defined in the appended claims.

What is claimed is:

1. A multi-slice X-ray CT apparatus provided with an X-ray generator and an X-ray detector disposed facing each other with a subject placed therebetween, said X-ray detector having a plurality of detector arrays for detecting X-rays from said X-ray generator, said apparatus rotating said X-ray generator and said X-ray detector to reconstruct a plurality of X-ray tomographic images in a direction of conveying said subject, said apparatus comprising:

a collimator for forming a slit defining a range of X-rays generated by said X-ray generator impinging upon said X-ray detector, and collimator regulator means for regulating the width of said slit corresponding to said direction of conveying the subject, wherein not all the widths of said X-ray detector arrays in said X-ray detector in said direction of conveying the subject are the same, and wherein the number of X-ray detector arrays in said X-ray detector is four, and the widths of the outer X-ray detector arrays in said conveying direction are larger than the widths of two center detector arrays in said conveying direction.

2. The multi-slice X-ray CT apparatus cited in claim 1, wherein the widths of said two center X-ray detector arrays in said conveying direction are the same, and the widths of said two outer X-ray detector arrays in said conveying direction are the same.

3. The multi-slice X-ray CT apparatus cited in claim 2, wherein said collimator regulating means further comprises means for regulating the position of said collimator in said conveying direction.

4. The multi-slice X-ray CT apparatus cited in claim 2, further comprising combining means for additively and selectively combining signals detected by adjacent X-ray detector arrays, wherein said combining means has at least four modes as follows:
mode 1: g1=s1, g2=s2, g3=s3, g4=s4;
mode 2: g1=s1, g2=s2+s3, g3=N/A, g4=s4;
mode 3: g1=s1+s2, g2=NA, g3=N/A, g4=s3+s4; and
mode 4: g1=s1+s2, g2=N/A, g3=s3, g4=s4, in which s1, s2, s3 and s4 represent respective signals detected by four X-ray detector arrays, and g1, g2, g3 and g4 represent output signals as the result of combination, and generates output signals in one of said modes based on a prespecified control signal.

5. The multi-slice X-ray CT apparatus cited in claim 1, wherein said collimator regulating means further comprises means for regulating the position of said collimator in said conveying direction.

6. The multi-slice X-ray CT apparatus cited in claim 1, further comprising combining means for additively and selectively combining signals detected by adjacent X-ray detector arrays, wherein said combining means has at least four modes as follows:
mode 1: g1=s1, g2=s2, g3=s3, g4=s4;
mode 2: g1=s1 g2=s2+s3, g3=N/A, g4=s4;
mode 3: g1=s1+s2, g2=N/A, g3=N/A, g4=s3+s4; and
mode 4: g1=s1+s2, g2=N/A, g3=s3, g4=s4,
in which s1, s2, s3 and s4 represent respective signals detected by four X-ray detector arrays, and g1, g2, g3 and g4 represent output signals as the result of combination, and generates output signals in one of said modes based on a prespecified control signal.

7. The apparatus of claim 1, wherein said collimator comprises a pair of parallel plates and rotatable means for controlling the distance between the parallel plates.

8. A method of controlling a multi-slice X-ray CT apparatus comprising:

an X-ray generator;

a collimator for forming a slit having a width corresponding to a range of generated X-rays;

an X-ray detector disposed facing said X-ray generator with a subject placed therebetween for detecting X-rays passing through said subject in a range defined by said slit in said collimator, said X-ray detector being comprised of a plurality of X-ray detector arrays in a direction of conveying said subject, not all of said X-ray detector arrays having the same width; and combining means for selectively adding a plurality of detected signals obtained by a plurality of X-ray detector arrays in said X-ray detector based on a control signal, and outputting signals in an output mode corresponding to said control signal, said method comprising:

a step of receiving instructive information from an external operating console;

a collimator regulating step for regulating the slid width in said conveying direction based on the received instructive information so that said collimator slit defines a specified range of impinging X-rays; and a step of supplying a control signal to said combining means based on the received instructive information; wherein the number of X-ray detector arrays constituting said X-ray detector is four, and the widths of the outer X-ray detector arrays in said conveying direction are larger than the widths of two center X-ray detector arrays in said conveying direction.

9. The method of controlling a multi-slice X-ray CT apparatus cited in claim 8, wherein the widths of said two center X-ray detector arrays in said conveying direction are the same, and the widths of said two outer X-ray detector arrays in said conveying direction are the same.

10. The method of controlling a multi-slice X-ray CT apparatus cited in claim 9, wherein said collimator regulating step further comprises a step of regulating the position of said collimator in said conveying direction.

11. The method of controlling a multi-slice X-ray CT apparatus cited in claim 10, wherein said combining means is configured to:

selectively add signals detected by adjacent X-ray detector arrays based on a control signal; and have at least four modes as follows:
mode 1: g1=s1, g2=s2, g3=s3, g4=s4;
mode 2: g1=s1, g2=s2+s3, g3=N/A, g4=s4;
mode 3: g1=s1+s2, g2=N/A, g3=N/A, g4=s3+s4; and
mode 4: g1=s1+s2, g2=N/A, g3=s3, g4=s4,
in which s1, s2, s3 and s4 represent respective signals detected by four X-ray detector arrays, and g1, g2, g3 and g4 represent output signals as the result of combination, and output signals in one output mode corresponding to said control signal.

12. The method of controlling a multi-slice X-ray CT apparatus cited in claim 9, wherein said combining means is configured to:

selectively add signals detected by adjacent X-ray detector arrays based on a control signal; and have at least four modes as follows:
mode 1: g1=s1, g2=s2, g3=s3, g4=s4;
mode 2: g1=s1, g2=s2+s3, g3=N/A, g4=s4;
mode 3: g1=s1+s2, g2=N/A, g3=N/A, g4=s3+s4; and
mode 4: g1=s1+s2, g2=N/A, g3=s3, g4=s4,
in which s1, s2, s3 and s4 represent respective signals detected by four X-ray detector arrays, and g1, g2, g3 and g4 represent output signals as the result of combination, and output signals in one output mode corresponding to said control signal.

13. The method of controlling a multi-slice X-ray CT apparatus cited in claim 8, wherein said combining means is configured to:

selectively add signals detected by adjacent X-ray detector arrays based on a control signal; and have at least four modes as follows:
mode 1: g1=s1, g2=s2, g3=s3, g4=s4;
mode 2: g1=s1, g2=s2 +s3, g3=N/A, g4=s4;
mode 3: g1=s1+s2, g2=N/A, g3=N/A, g4=s3+s4; and
mode 4: g1=s1+s2, g2=N/A, g3=s3, g4=s4,
in which s1, s2, s3 and s4 represent respective signals detected by four X-ray detector arrays, and g1, g2, g3 and g4 represent output signals as the result of combination, and output signals in one output mode corresponding to said control signal.

14. The method of claim 8, wherein said collimator comprises a pair of parallel plates and rotatable means for controlling the distance between the parallel plates, and wherein said collimator regulating step comprises causing said rotatable means to control the distance between said pair of parallel plates thereby to regulate the slit width.

15. A multi-slice X-ray CT apparatus provided with an X-ray generator and an X-ray detector disposed facing each other with a subject placed therebetween, said X-ray detector having a plurality of detector arrays for detecting X-rays from said X-ray generator, said apparatus rotating said X-ray generator and said X-ray detector to reconstruct a plurality of X-ray tomographic images in a direction of conveying said subject, said apparatus comprising:

a collimator for forming a slit defining a range of X-rays generated by said X-ray generator impinging upon said X-ray detector, said collimator comprising a pair of parallel plates and rotatable means for controlling the distance between said pair of parallel plates; and means for regulating the width of said slit corresponding to said direction of conveying the subject by causing said rotatable means to regulate the distance between said pair of parallel plates; wherein the widths of said X-ray detector arrays in said X-ray detector in said direction of conveying the subject are at least two different widths.

16. The apparatus of claim 15, further comprising means for regulating the position of said collimator in said conveying direction.

17. The multi-slice X-ray CT apparatus cited in claim 16, further comprising combining means for additively and selectively combining signals detected by adjacent X-ray detector arrays, wherein said combining means has at least four modes as follows:
mode 1: g1=s1, g2=s2, g3=s3, g4=S4;
mode 2: g1=s1, g2 =s2+s3, g3=N/A, g4=s4;
mode 3: g1=s1+s2, g2=N/A, g3=N/A, g4=s3+s4; and
mode 4: g1=s1+s2, g2=N/A, g3=s3, g4=s4, in which s1, s2, s3 and s4 represent respective sIgnals detected by four X-ray detector arrays, and g1, g2, g3 and g4 represent output signals as the result of combination, and generates output signals in one of said modes based on a prespecified control signal.

18. A method of controlling a multi-slice X-ray CT apparatus comprising:

an X-ray generator;

a collimator for forming a slit having a width corresponding to a range of generated X-rays, said collimator comprising a pair of parallel plates and rotatable means for controlling the distance between said pair of parallel plates;

an X-ray detector disposed facing said X-ray-generator with a subject placed therebetween for detecting X-rays passing through said subject in a range defined by said slit in said collimator, said X-ray detector being comprised of a plurality of X-ray detector arrays in a direction of conveying said subject, there being at least two different widths of said X-ray detector arrays; and means for selectively adding a plurality of detected signals obtained by a plurality of X-ray detector arrays in said X-ray detector based on a control signal, and outputting signals in an output mode corresponding to said control signal, said method comprising the steps of:

receiving instructive information from an external operating console;

causing said rotatable means for controlling to regulate the distance between said pair of parallel plates to thereby regulate the slit width in said conveying direction based on the received instructive information so that said collimator slit defines a specified range of impinging X-rays; and supplying a control signal to said combining means based on said received instructive information.

* * * * *